(12) United States Patent  
Cohen

(10) Patent No.: US 6,426,859 B1
(45) Date of Patent: Jul. 30, 2002

(54) STATIC DISSIPATIVE/ANTI-STATIC EXPANSION/FIXED SIZE BRACELET/BUCKLE COMBINATION

(75) Inventor: Leonard Cohen, Southboro, MA (US)

(73) Assignee: Static Solutions, Inc., Marlborough, MA (US)

( * ) Notice: Subject to any disclaimer, the term of this patent is extended or adjusted under 35 U.S.C. 154(b) by 0 days.

(21) Appl. No.: 09/558,579

(22) Filed: Apr. 26, 2000

Related U.S. Application Data

(60) Provisional application No. 60/131,820, filed on Apr. 29, 1999.

(51) Int. Cl.[7] .................................................. H05F 3/02
(52) U.S. Cl. ........................ 361/220; 361/212; 57/901
(58) Field of Search ................................ 361/212, 220, 361/223; 57/901

(56) References Cited

U.S. PATENT DOCUMENTS

| | | | |
|---|---|---|---|
| 3,857,397 A | 12/1974 | Brosseau | |
| 4,096,688 A | 6/1978 | Rieth | |
| 4,296,532 A | 10/1981 | Ho | |
| 4,373,175 A | 2/1983 | Mykkanen | |
| 4,375,713 A | 3/1983 | Bert et al. | |
| 4,398,277 A | 8/1983 | Christiansen et al. | |
| 4,402,560 A | 9/1983 | Swainbank | |
| 4,459,633 A | 7/1984 | Vandermark | |
| 4,475,141 A | 10/1984 | Antonevich | |
| 4,475,142 A | 10/1984 | Sparks | |
| 4,577,256 A | 3/1986 | Breidegam | |
| 4,596,053 A | 6/1986 | Cohen et al. | |
| 4,605,984 A | 8/1986 | Fiedler | |
| 4,639,825 A | 1/1987 | Breidegam | |
| 4,654,748 A | 3/1987 | Rees | |
| 4,662,695 A | 5/1987 | Gordon et al. | |
| 4,664,158 A | 5/1987 | Sands | |
| 4,676,561 A | 6/1987 | Barrett, II | |
| 4,745,519 A | 5/1988 | Breidegam | |
| 4,755,144 A | 7/1988 | Gordon et al. | |
| 4,782,425 A | 11/1988 | Breidegam | |
| 4,813,459 A | * 3/1989 | Breidegam ................ 139/421 |
| 4,816,964 A | 3/1989 | Weiss | |
| 4,845,585 A | 7/1989 | Weiss | |
| 4,847,729 A | 7/1989 | Hee | |
| 4,878,148 A | 10/1989 | Hee | |
| 5,018,044 A | 5/1991 | Weiss | |
| 5,036,423 A | 7/1991 | Williams | |
| 5,134,528 A | 7/1992 | Sato | |
| 5,568,351 A | 10/1996 | West et al. | |

* cited by examiner

Primary Examiner—Kim Huynh
(74) Attorney, Agent, or Firm—Peter F. Corless; Lisa S. Hazzard; Edwards & Angell, LLP

(57) ABSTRACT

Grounding straps for removing static electricity from the wearer. More particularly, the straps have a conductive interior and an anti-static or static dissipative exterior. The anti-static exterior has an electrical resistance of between $10^6$ and $10^{12}$ ohms which will not create static electricity when rubbed and will not wear off with use.

32 Claims, 1 Drawing Sheet

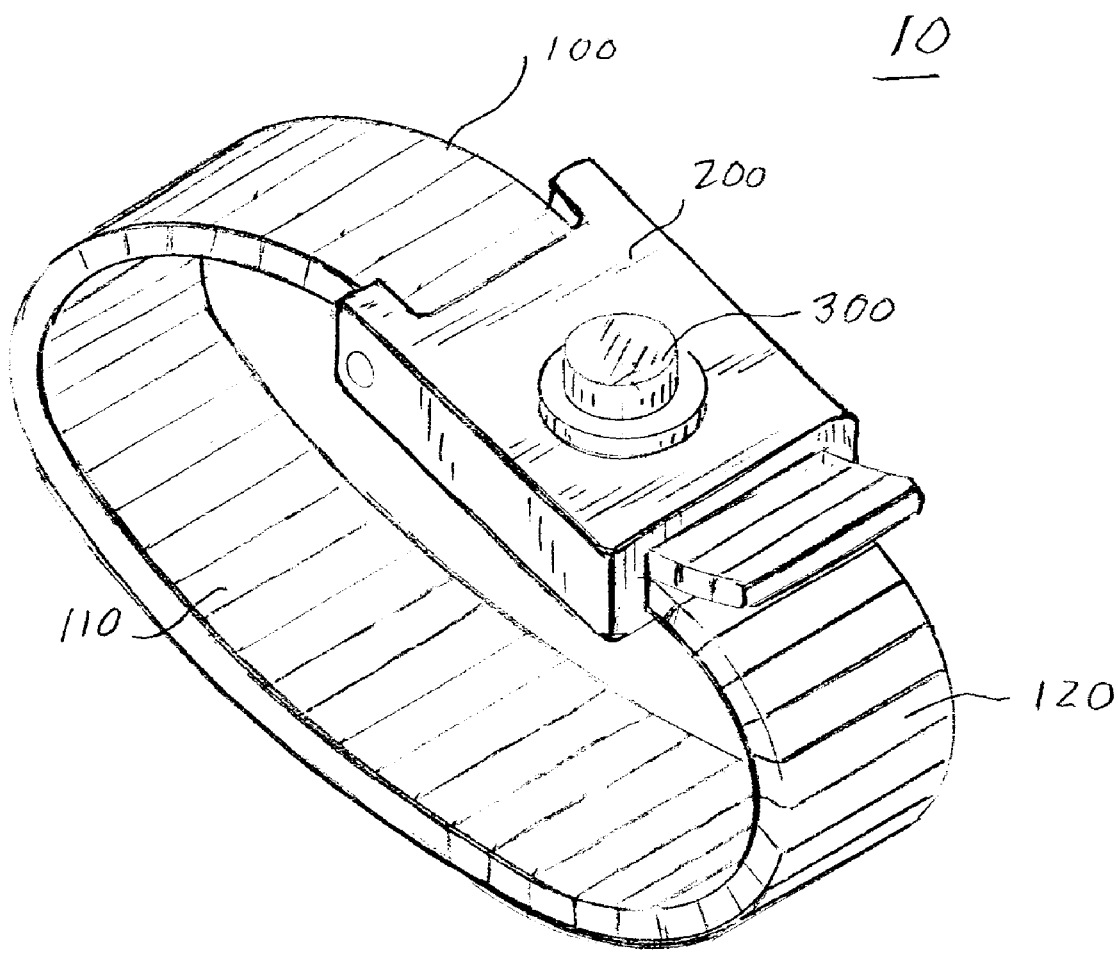

STATIC DISSIPATIVE/ANTI-STATIC EXPANSION/FIXED SIZE BRACELET/ BUCKLE COMBINATION

This application claims the benefit of U.S. Provisional Application No. 60/131,820, filed Apr. 29, 1999, which is incorporated herein by reference.

BACKGROUND OF THE INVENTION

1. Field of the Invention

The present invention relates to an electrically conductive grounding strap which can drain or wick static electrical charge from the wearer. In particular, the invention relates to wrist straps and buckles made of an anti-static or static dissipative material.

2. Background

As reported in U.S. Pat. No. 4,577,256, static electricity provides problems in the electronics and other industries, particularly with the advent of integrated circuits and other microelectronic components. Components such as integrated circuits, for instance, may be disabled or destroyed by over-voltage or power density resulting from static electricity. Certain junctions in such circuits can be destroyed by as little as a 50-volt potential, which radically changes the doping structure in their lattices. Power densities resulting from excessive potential and imperfections in a silicon circuit layout or structure can vaporize or radically alter the silicon substrate and thus impair or destroy a circuit's performance. Yet a person walking on a carpet on a dry day can accumulate as much as 30,000 volts of potential, and he can triboelectrically generate thousands of volts by simply changing his position in his chair or handling a styrofoam cup.

Such a person can inadvertently discharge such static electric potential into a circuit or component by touching it and causing overvoltage or excessive power density. Additionally, the potential in such a person's body can induce a charge in a circuit that can later cause overvoltage or excessive power density when the circuit is subsequently grounded. More and more frequently, therefore, personnel in industries in which integrated circuits and other microelectronic components are handled or assembled are taking measures to limit the failure rate of those circuits and components by attempting to keep both them and their environment at a zero electrical potential. Such measures include providing workers and work stations with antistatic carpet, conductive or dissipative grounded desk top work surfaces; hot air ion generators which emit ions to neutralize static charges; and grounding straps to keep workers at zero potential.

A person working on microelectronic components or integrated circuits may be completely unaware that he has accumulated minor static electrical discharges, and may therefore unknowingly be in a position to disable circuits on which he is working or which he is handling. If he is wearing a grounding strap which is not sufficiently effective, he may be unaware that electrical discharges transmitted from his fingers are disabling these circuits. A typical person cannot sense a static electrical discharge of less than approximately 3,500 volts. No one may discover that the circuits have been disabled or damaged until hours, days or weeks later, when the circuits have been placed in components or devices which fail in the field. Removal and repair or replacement of these circuits once in the field is far costlier than avoiding potential failure while the wearer is handling the circuits. Thus, the wearer's employer typically must depend upon the effectiveness of the wrist strap to maintain a lower failure rate of such electronic circuits and components, by maintaining continuous electrical contact with the wearer's wrist.

Over the years, various types of grounding straps have been developed in an effort to maximize the functionality and comfort of the device. The straps may be made of fabric, elastic fabric, metal or metal expansion type bands. The bands may be adjustable or non-adjustable and available in different sizes. The bands can be slid on over the hand or may be fastened via snaps, velcro, buckles, etc. Straps have also been developed which contain a monitor for detecting electrical continuity between the band and the ground.

The term "conductive" herein, and according to its customary usage in the art, means an electrical resistance of between zero and $10^5$ ohms. Similarly, "dissipative" means a resistance of between $10^5$ and $10^{12}$ ohms and "insulative" means a resistance of more than $10^{12}$ ohms.

A grounding strap must have several features in order to perform its grounding function effectively. First, it must ensure that the wearer's skin is electrically connected to the ground. This connection is typically accomplished by a conductive surface on the inside of a strap contacting the skin. The conductive surface is electrically connected to a grounding cord which leads from the strap to a grounded electrical connection. The electrical resistance of the cord resistor is typically about 1 megaohm whereas the resistance of the conductive material on the interior of the strap is well below this value.

Second, the exteriors of any metal band or buckle used on a grounding strap must be encapsulated or coated to prevent electrical shock to the person wearing the bracelet and to prevent damage to the device being worked upon due to a too rapid static discharge. Typically, encapsulation is carried out by applying a plastic film molded from an insulative polymer, for example TEDLAR® from Dupont, or a paint containing an insulative material (i.e. an electrical resistance of greater than $10^{12}$ ohms). All prior art grounding strap inventions contain insulative exteriors. In fact, the regulatory agency of the static control industry states in the EOS/ESD S-1 that the outside of the grounding strap and buckle should be insulative.

However, the materials currently being used on the exterior of grounding straps and buckles are not conductive due to safety concerns for the wearer. Thus, the risk of accumulation of static electricity on the surface of the strap or buckle is a serious problem since this exterior electricity cannot be dissipated though electrical grounding and neutralization of surface static by ionization is not feasible or practical. Ideally, the electrical resistance of the exterior of the grounding strap should be between $10^6$ and $10^{12}$ ohms and non tribogenerative. If the resistance is greater than $10^{12}$ ohms, the wearer might cause device damage if the static strap or buckle comes in close proximity to the device, especially if the strap or buckle contains static electricity on the surface due to tribogeneration. For example, TEDLAR® is an insulating polyvinylidenefluoride film laminate which has been used to encapsulate the exterior of metallic grounding bands. However, when rubbed against other materials, TEDLAR® will tribogenerate a static charge which may dissipate and cause static electric damage due to too rapid a discharge or secondary field generation. Further, if the electrical resistance of the exterior of the strap or buckle is less than $10^6$ ohms, the wearer is at risk of bypassing the current limiting resistor and for receiving an electrical shock.

Devices at risk from static electricity are becoming more and more static sensitive. Thus, it is increasingly important and desirable to develop grounding straps which are more effective at dissipating static electrical charges.

See also: Antonevich et al., U.S. Pat. No. 4,475,142; Barrett, II et al., U.S. Pat. No. 4,676,561; Bertet et al., U.S. Pat. No. 4,375,713; Breidegam et al., U.S. Pat. No. 4,577,256; Breidegam et al. U.S. Pat. No. 4,639,825; Breidegam et al., U.S. Pat. No. 4,745,519; Breidegam et al., U.S. Pat. No. 4,782,425; Brosseau et al., U.S. Pat. No. 3,857,397; Burke et al., U.S. Pat. No. 3,596,134; Christansen et al., U.S. Pat. No. 4,398,277; Cohen et al., U.S. Pat. No. 4,596,053; Fiedler et al., U.S. Pat. No. 4,605,984; Freitag et al., U.S. Pat. No. 1,940,491; Gandelman et al., U.S. Pat. No. 3,685,106; Gordon et al., U.S. Pat. No. 4,662,695; Gordon et al., U.S. Pat. No. 4,755,144; Hee et al., U.S. Pat. No. 4,847,729; Hee et al., U.S. Pat. No. 4,878,148; Ho et al., U.S. Pat. No. 4,296,532; Mykkanen et al., U.S. Pat. No. 4,373,175; O'Neill et al., U.S. Pat. No. 2,588,655; Otten et al., U.S. Pat. No. 1,760,913; Rees et al., U.S. Pat. No. 4,654,748; Rieth et al., U.S. Pat. No. 4,096,688; Sands et al., U.S. Pat. No. 4,664,158; Swainbank et al., U.S. Pat. No. 4,402,560; Vandermark et al., U.S. Pat. No. 4,459,633; Weiss et al., U.S. Pat. No. 4,816,964; Weiss et al., U.S. Pat. No. 4,845,585; Weiss et al., U.S. Pat. No. 5,018,044; Weiss et al., U.S. Pat. No. 5,134,528; West et al., U.S. Pat. No. 5,568,351; Williams et al., U.S. Pat. No. 5,036,423.

SUMMARY OF THE INVENTION

The present invention provides a method and apparatus for removing static electricity from a person.

More particularly, the present invention provides a conductive body strap which may be attached to a ground so as to safely drain static electricity from the wearer. The strap has a conductive interior and an anti-static, static dissipative, or non-tribogenerative exterior. The anti-static exterior has an electrical resistance of between $10^6$ and $10^{12}$ ohms which will not create static electricity when rubbed and will not wear off over time.

The straps optionally contain fasteners and both the strap and fastener may be fabricated from homogenous, coated or laminated materials. The straps may be composed of anti-static fabric or metal encapsulated in anti-static or static dissipative paint or plastic. The fasteners may be snaps, velcro or buckles composed of anti-static or static dissipative plastic or may be composed of metal encapsulated in anti-static or static dissipative paint or plastic.

In a preferred embodiment, the strap fits around the wrist and contains a buckle so as to adjust to fit multiple users. The strap is fabricated from non nickel containing stainless steel and is coated with an anti-static plastic overlay. The strap is secured with a plastic buckle that is composed entirely of an anti-static polymer. The exterior of the buckle contains a snap which can electrically connect the strap to a resistor fitted grounding cord through which the static electricity may be drained to ground.

Other aspects and embodiments of the invention are disclosed infra.

BRIEF DESCRIPTION OF THE DRAWING

For a fuller understanding of the nature and desired objects of the present invention, reference is made to the following detailed description taken in conjunction with accompanying drawing figures wherein like reference character denote corresponding parts throughout several views wherein:

The figure is a representation of a conductive body strap according to an embodiment of the invention.

DETAILED DESCRIPTION OF THE INVENTION

Referring now to the figure of the drawing wherein like reference characters refer to like parts, there is shown a conductive body strap 10 including a strap 100 and an electrical connector 300 which is connectable to a ground. The electrical connector 300 is affixed to the exterior of the strap 100. The strap is constructed so that the interior surface 110 is conductive and the exterior surface 120 is static dissipative or anti-static.

The strap 100 is preferably fabricated of cloth or metal. Cloth straps may be made from static dissipative material and may be elastic or non-elastic material. Metal straps may be expansion type bands composed of multiple interconnecting links or may be constructed as a mesh type band. Metal bands are preferably made from stainless steel that is essentially free of nickel so as to avoid possible irritation to the wearer. When metals other than stainless steel are used, the interior of the band 110 is preferably coated with silver or gold.

The strap 100 is preferably constructed so as to fit around the wrist and may be adjustable or non-adjustable. Non-adjustable straps may be slid on over the hand to fit around the wrist and may come in a multitude of sizes so as to fit differently sized users. Adjustable straps will preferably contain a fastener 200 such as a snap, a series of snaps, a velcro-type closure, a buckle, etc. A buckle fastening may be fixed at a particular location or may be adjustable so as to fit multiple users with one sized band. Snap and buckle fasteners may be made of plastic or metal.

Metal straps and buckles are preferably coated, encapsulated or laminated with an anti-static material having an electrical resistance of between $10^6$ and $10^{12}$ ohms. Anti-static materials are known in the art and include, for example, epoxy, urethane or UV cured acrylic. The exterior of metal straps and buckles may also be painted with anti-static material. Plastic snaps or buckles used as fasteners for the strap may be molded entirely of an anti-static polymer or may be coated, encapsulated or laminated with an anti-static material. The antistatic plastic must be permanent, non-irritating to the wearer and must not outgas. Particularly preferred polymers are PERMASTAT® polycarbonate from RTP corporation, STAT-RITE® from B.F. Goodrich and PELESTAT® from Tomen Corporation.

The electrical connector 300 affixed to the exterior of the strap is preferably a male or female snap which can be attached to a resistor fitted grounding cord through which static electricity may be safely drained to ground. However, this is not meant to be a limitation and any other type of fastener which provides a suitable connection to the grounding cord may be used. The strap may also contain a monitor for detecting the electrical continuity between the band and the ground.

In a particularly preferred embodiment, the strap 100 is a metal expansion type bracelet with an anti-static plastic overlay which is injection molded and attached to the exterior of the non nickel containing stainless steel expansion band. The buckle 200 is entirely composed of an anti-static plastic material and can be opened and reclosed to adjust the bracelet depending on the size of the wearer. The buckle preferably contains upward ridges on the interior surface to prevent slippage of the buckle on the expansion links during usage. The electrical attachment element 300 located on the exterior of the buckle is a male or female snap which can be attached to a resistor fitted grounding cord. When the buckle is in the closed position, the attachment element is in electrical contact with the non nickel containing stainless steel metal of the expansion bracelet through a conductive clip or spring which is located within the buckle.

Although a preferred embodiment of the invention has been described using specific terms, such description is for illustrative purposes only, and it is to be understood that changes and variations may be made without departing from the spirit or scope of the following claims.

What is claimed is:

1. A conductive body strap for connecting a person's body to a ground comprising:
    a strap having a conductive interior and an anti-static exterior; and
    an electrical connector affixed to the exterior of said strap which is connectable to a ground.

2. The conductive body strap of claim 1, wherein the strap is composed of static dissipative cloth.

3. The conductive body strap of claim 2, wherein the static dissipative cloth is elastic.

4. The conductive body strap of claim 1, wherein the strap is composed of metal.

5. The conductive body strap of claim 4, wherein the strap is composed of stainless steel.

6. The conductive body strap of claim 5, wherein the stainless steel strap is essentially free of nickel.

7. The conductive body strap of claim 4, wherein the interior of the strap is plated with silver or gold.

8. The conductive body strap of claim 4, wherein the metal strap is an expansible band.

9. The conductive body strap of claim 4, wherein the metal band is coated or encapsulated with an anti-static material.

10. The conductive body strap of claim 9, wherein the anti-static material has an electrical resistance of between $10^6$ and $10^{12}$ ohms.

11. The conductive body strap of claim 9, wherein the anti-static material is epoxy, urethane or UV cured acrylic.

12. The conductive body strap of claim 4, wherein the exterior of the metal band is painted with an anti-static material.

13. The conductive body strap of claim 1, wherein the strap is non-adjustable and may be slid on over the hand to fit around the wrist.

14. The conductive body strap of claim 1, wherein the strap is adjustable.

15. The conductive body strap of claim 1, which further comprises a fastening device.

16. The conductive body strap of claim 15, wherein the fastening device is one snap, multiple snaps, velcro or a buckle.

17. The conductive body strap of claim 15, wherein the fastening device is a buckle.

18. The conductive body strap of claim 17, wherein the buckle is composed of a static dissipative polymer.

19. The conductive body strap of claim 18, wherein the static dissipative polymer is the polycarbonate PERMASTAT®.

20. The conductive body strap of claim 18, wherein the static dissipative polymer is STAT-RITE®.

21. The conductive body strap of claim 18, wherein the static dissipative polymer is PELESTAT®.

22. The conductive body strap of claim 17, wherein the buckle is composed of metal.

23. The conductive body strap of claim 22, wherein the buckle is composed of stainless steel.

24. The conductive body strap of claim 23, wherein the stainless steel buckle is essentially free of nickel.

25. The conductive body strap of claim 22, wherein the interior of the buckle is plated with silver or gold.

26. The conductive body strap of claim 22, wherein the metal buckle is coated or encapsulated with an anti-static material.

27. The conductive body strap of claim 26, wherein the anti-static material has an electrical resistance of between $10^6$ and $10^{12}$ ohms.

28. The conductive body strap of claim 26, wherein the anti-static material is epoxy, urethane or UV cured acrylic.

29. The conductive body strap of claim 26, wherein the exterior of the metal buckle is painted with an anti-static material.

30. The conductive body strap of claim 1, wherein the electrical connector is a male or female snap which may be attached to a resistor fitted grounding cord through a corresponding snap on said cord.

31. The conductive body strap of claim 1, wherein the strap is constructed so as to fit around the wrist.

32. A method for draining static electricity from a person, comprising:
    contacting the persons skin with a conductive body strap comprising
        a strap having a conductive interior and an anti-static exterior, and
        an electrical connector affixed to the exterior of the strap which is connectable to a ground; and
    draining the static electricity to ground through a resistor fitted grounding cord that is electrically connected to the body conductive strap.

* * * * *